United States Patent
Zhang (10) Patent No.: US 10,882,817 B2
(45) Date of Patent: *Jan. 5, 2021

(54) ACETYLSALICYLIC ACID DERIVATIVE CRYSTAL, ITS PREPARATION METHOD AND USE

(71) Applicant: Zhejiang Yuejia Pharmaceuticals Co., Ltd, Deqing County (CN)

(72) Inventor: Jing Zhang, Shanghai (CN)

(73) Assignee: Zhejiang Yuejia Pharmaceuticals Co., Ltd, Deqing County (CN)

( * ) Notice: Subject to any disclaimer, the term of this patent is extended or adjusted under 35 U.S.C. 154(b) by 17 days.

This patent is subject to a terminal disclaimer.

(21) Appl. No.: 16/676,575

(22) Filed: Nov. 7, 2019

(65) Prior Publication Data

US 2020/0123098 A1 Apr. 23, 2020

Related U.S. Application Data

(62) Division of application No. 15/562,222, filed as application No. PCT/CN2016/075753 on Mar. 7, 2016, now Pat. No. 10,532,973.

(30) Foreign Application Priority Data

Apr. 1, 2015 (CN) .......................... 2015 1 0151946

(51) Int. Cl.
C07C 219/14 (2006.01)
A61K 31/621 (2006.01)
C07C 213/06 (2006.01)

(52) U.S. Cl.
CPC .......... *C07C 219/14* (2013.01); *A61K 31/621* (2013.01); *C07C 213/06* (2013.01); *C07B 2200/13* (2013.01)

(58) Field of Classification Search
CPC ... C07C 219/14; C07C 213/06; A61K 31/621; C07B 2200/13
USPC ...................................................... 514/166
See application file for complete search history.

(56) References Cited

U.S. PATENT DOCUMENTS 3,365,483 A 1/1968 Zofia Jerzmanowska et al.

FOREIGN PATENT DOCUMENTS

CN 104276962 A 1/2015
JP 2009542797 A 12/2009
WO 2014139161 A1 9/2014

OTHER PUBLICATIONS

Cancer [online], [retrieved on Jul. 6, 2007] Retrieved from the Internet, URL: http://www.nlm.nih.gov/medlineplus/cancer.html (Year: 2007).*

Lala et al., Role of nitric oxide in tumor progression: Lessons from experimental tumors, Cancer and Metastasis Reviews (1998), 17, 91-106 (Year: 1998).*

Golub et al., Molecular Classification of Cancer: Class Discovery and Class Prediction by Gene Expression Monitoring, Science (1999), vol. 286, 531-537 (Year: 1999).*

International Search Report and Written Opinion dated Jun. 3, 2016, for corresponding International Application No. PCT/CN2016/075753; International Filing Date: Mar. 7, 2016 consisting of 4-pages.

Lespagnol et al., "Several New Derivatives of Aspirin," Bulletin de la Societe de Pharmacie de Lille; vol. 1, pp. 33-41, 1967; consisting of 2-pages.

Chinese Office Action and English Translation dated Mar. 11, 2019, for corresponding International Application No. CN201510151946.2; consisting of 20-pages.

Japanese Office Action dated Jul. 13, 2018, for corresponding International Application No. JP2017-567519; Filing Date: Mar. 7, 2016, consisting of 3-pages.

"Production Technique of Solid Formulation," CMC Publications Co., Ltd., Jan. 27, 2003, pp. 9 and 12-13.

Byrn, et al., "Pharmaceutical Solids: A Strategic Approach to Regulatory Considerations," Pharmaceutical Research, vol. 12., No. 7, 1995, pp. 945-954.

"Solvent Handbook," Kodansha Co., Ltd., Sep. 1, 1985, pp. 46-51.

Bavin, "Polymorphism in Process Development," Process Development, Chemistry & Industry, Aug. 21, 1989, pp. 527-529.

European Search Report dated Nov. 14, 2018, for corresponding Application No. EP16771223.1, Filing Date: Mar. 7, 2016, consisting of 6-pages.

Fred Kagan et al., "Reactions in the Salicylic Acid Series. A New Rearrangement of Acylsalicylic Acid Derivatives," Journal of the American Chemical Society, vol. 81, No. 8, Apr. 1, 1959, pp. 1986-1991.

(Continued)

*Primary Examiner* — Kristin A Vajda (74) *Attorney, Agent, or Firm* — Christopher & Weisberg, P.A.

(57) ABSTRACT

A disclosed are an acetylsalicylic acid derivative, i.e. a 2-(diethylamino)ethyl 2-acetoxy-benzoate hydrochloride crystal, and a preparation method and use thereof. The X-ray powder diffraction (XRPD) pattern of the crystal has characteristic peaks at the following 2θ angle: 11.0°±0.2°, 20.6°±0.2°, 25.1°±0.2°, 8.2°±0.2°, 16.5°±0.2°, 13.4°±0.2°, 25.4°±0.2°.

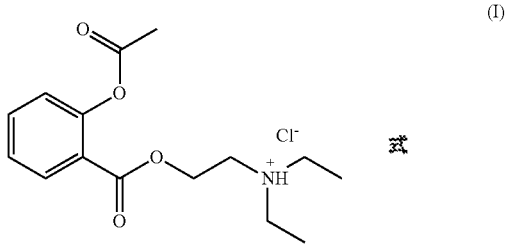

(I)

11 Claims, 2 Drawing Sheets

(56) References Cited

OTHER PUBLICATIONS

Mino R. Caira et al., "Crystalline Polymorphism of Organic Compounds," Topics in Current Chemistry, vol. 198, Jan. 1, 1998, pp. 163-208.

* cited by examiner

ACETYLSALICYLIC ACID DERIVATIVE CRYSTAL, ITS PREPARATION METHOD AND USE

CROSS-REFERENCE TO RELATED APPLICATION

This application is a divisional of U.S. National Stage patent application Ser. No. 15/562,222, filed Apr. 20, 2018, entitled "ACETYLSALICYLIC ACID DERIVATIVE CRYSTAL, ITS PREPARATION METHOD AND USE," which claims priority to, International Application Number PCT/CN2016/075753, filed Mar. 7, 2016, entitled "ACETYLSALICYLIC ACID DERIVATIVE CRYSTAL, ITS PREPARATION METHOD AND USE," which is related to and claims priority to Chinese Application Number 201510151946.2, filed Apr. 1, 2015, the entirety of all of which are incorporated herein by reference.

FIELD

The present invention relates to the chemical raw pharmaceutical field and, more particularly, to an acetylsalicylic acid derivative 2-(diethylamino)ethyl 2-acetoxybenzoate hydrochloride crystal, and its preparation method and use.

BACKGROUND

Aspirin, also known as acetylsalicylic acid, was first synthesized in 1853 and applied in clinical treatments in 1899. Aspirin has a variety of pharmaceutical efficacies, and aspirin can have an effect of alleviating headache in a short term by angiectasis, and can be therefore used for analgesia and antipyresis. Aspirin is the first choice drug for the treatment of rheumatic fever, and after administration, antipyresis and inflammation reduction can be achieved, such that articular symptoms are improved, and the erythrocyte sedimentation rate is reduced. In addition to rheumatoid arthritis, the product is also used for treating rheumatoid arthritis, can improve symptoms, and create conditions for a further treatment. In addition, aspirin is used for musculoskeletal pain disease of osteoarthritis, ankylosing spondylitis, juvenile arthritis and other non-rheumatic inflammations, and can also relieve symptoms. Aspirin has an inhibiting effect on platelet aggregation and can thus prevent thrombosis, and clinically, aspirin can be used for preventing transient ischemic attack, myocardial infarction, atrial fibrillation, cardiac valve prosthesis or other postoperative thrombosis, and can also be used for treating unstable angina pectoris. Aspirin can also be used for reducing mucocutaneous lymphnode syndrome (Kawasaki disease). It is also found from studies that aspirin works in terms of the prevention of colon cancer, rectal cancer, esophageal cancer, etc. Therefore, the therapeutic use of aspirin is very valuable.

However, the oral administration of aspirin tends to result in gastrointestinal adverse reactions. The most major reactions include indigestion, stomach and duodenal hemorrhages, gastric ulcer, gastritis and other symptoms. Therefore, researchers have been trying all the time to study aspirin derivatives of other administration routes, in order to reduce or avoid the gastrointestinal adverse reactions caused by the oral administration of aspirin.

Chinese patent CN 101484415 B discloses a water-soluble aspirin prodrug (an acetylsalicylic acid derivative), and in the treatment, the prodrug may be administered transdermally into the body, avoiding the gastrointestinal adverse reactions caused by the common oral administration of aspirin.

However, the above-mentioned patent does not disclose any compound crystal form of the water-soluble aspirin prodrug. The study of solid drug crystal form facilitates the control of the stability of the drug during preparation and storage. The determination of a preparation process according to the characteristics of a crystal form to improve the performance of a solid pharmaceutical preparation can effectively ensure the drug inter-batch equivalence in production. Therefore, obtaining the crystal form of the compound is an important measure to ensure the quality of the drug.

SUMMARY

The present invention provides, for the first time, an acetylsalicylic acid derivative 2-(diethylamino)ethyl 2-acetoxybenzoate hydrochloride crystal.

Another object of the present invention is to provide a method for preparing said acetylsalicylic acid derivative 2-(diethylamino)ethyl 2-acetoxybenzoate hydrochloride crystal.

A further object of the present invention is to provide use of said 2-(diethylamino)ethyl 2-acetoxybenzoate hydrochloride crystal.

A fourth object of the present invention is to provide a pharmaceutical composition containing the 2-(diethylamino)ethyl 2-acetoxybenzoate hydrochloride crystal.

In a first aspect of the present invention, there is provided a 2-(diethylamino)ethyl 2-acetoxybenzoate hydrochloride crystal having a chemical structure as represented by formula I, wherein the X-ray powder diffraction (XRPD) pattern of said crystal has characteristic peaks at the following 2θ angles: 11.0°±0.2°, 20.6°±0.2°, 25.1°±0.2°, 8.2°±0.2°, 16.5°±0.2°, 13.4°±0.2°, and 25.4°±0.2°;

I

In another preferred embodiment, the X-ray powder diffraction (XRPD) pattern of said crystal further has a characteristic peak at the following 2θ angles: 10.8°±0.2°.

In another preferred embodiment, the X-ray powder diffraction (XRPD) pattern of said crystal further has characteristic peaks at the following 2θ angles: 22.8°±0.2°, 30.4°±0.2°, 19.2°±0.2°, 17.6°±0.2°, 10.6°±0.2°, 23.0°±0.2°, 35.7°±0.2°, 27.9°±0.2°, 18.2°±0.2°, 24.8°±0.2°, and 22.1°±0.2°.

Figure 1:
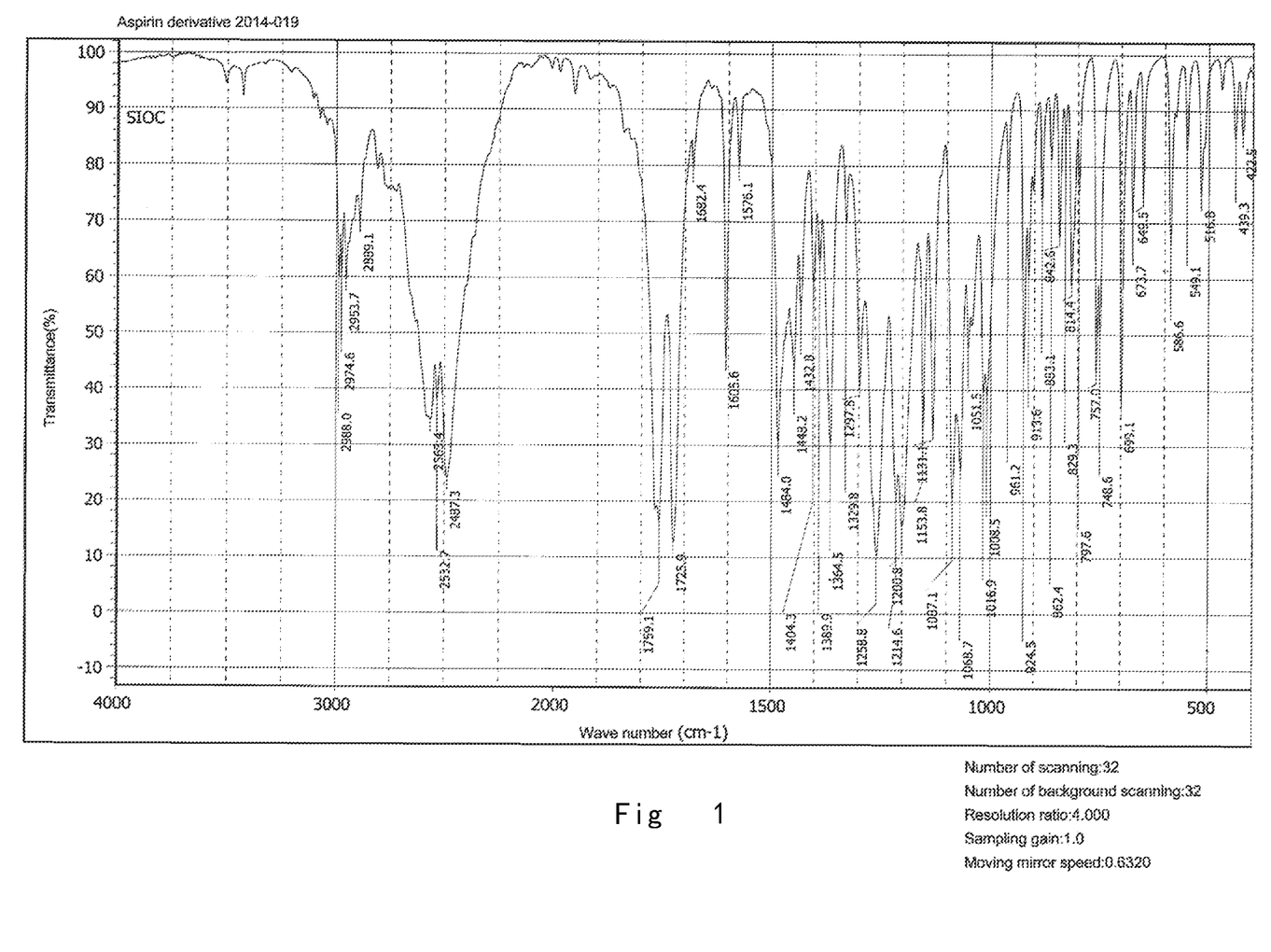
FIG. 1 shows an infrared absorption spectrum of the 2-(diethylamino)ethyl 2-acetoxybenzoate hydrochloride crystal as described in the present invention.

In another preferred embodiment, the infrared absorption spectrum of said crystal has absorption peaks at 2988.0 cm-1, 2974.6 cm-1, 2953.7 cm-1, 2889.1 cm-1, 1725.9 cm-1, 1759.1 cm-1, 1605.6 cm-1, 1576.1 cm-1, 1484.0 cm-1, 1448.2 cm-1, 1389.9 cm-1, 1068.7 cm-1, 1087.1 cm-1, 757.0 cm-1, and a range of 2487.3 cm-1-2563.4 cm-1; more preferably, said crystal has an infrared spectroscopy as shown in FIG. 1.

In a second aspect of the present invention, there is provided a 2-(diethylamino)ethyl 2-acetoxybenzoate hydrochloride crystal having a chemical structure as represented by formula I, said crystal being orthorhombic, and having lattice parameters, as determined by X-ray single crystal diffraction: a=16.01 Å±0.01 Å, b=7.17 Å±0.01 Å, c=28.86 Å±0.01 Å, and α=β=γ=90°;

I

In another preferred embodiment, said crystal, as determined by X-ray single crystal diffraction, further comprises the following characteristics:
a crystallographic space group: Pbca;
a unit lattice volume: V=3311.4 Å3±1.0 Å3;
a crystal size: 0.211×0.176×0.112 mm3;
a crystal density: 1.267 mg/m3;
a number of asymmetrical units in lattice: 8; and
a number of electrons in a unit cell: F(0000)=1344.

In a third aspect of the present invention, there is provided a method for preparing the 2-(diethylamino)ethyl 2-acetoxybenzoate hydrochloride crystal provided by the present invention as described above, said method comprising the steps of:
(1) mixing a crude 2-(diethylamino)ethyl 2-acetoxybenzoate hydrochloride raw material with anhydrous acetonitrile, and completely dissolving the raw materials to obtain a solution; and
(2) cooling the solution to 0-30° C. to precipitate the 2-(diethylamino)ethyl 2-acetoxybenzoate hydrochloride crystal provided by the present invention as described above.

In another preferred embodiment, the final mass-volume ratio of the crude 2-(diethylamino)ethyl 2-acetoxybenzoate hydrochloride raw material to the anhydrous acetonitrile is 1: 2-1:20 w/v, more preferably 1: 4-1:10 w/v.

In another preferred embodiment, heating is required in said dissolution process; more preferably, heating to refluxing anhydrous acetonitrile is required in said dissolution process.

In another preferred embodiment, the crystal precipitated in step (2) is filtered and dried; Suction filtration is used for said filtration method; and said drying is carried out by vacuum drying, more preferably rotary vacuum drying.

In another preferred embodiment, the solution is cooled to 4-25° C. for the crystal precipitation.

In a fourth aspect of the present invention, there is provided a use of the 2-(diethylamino)ethyl 2-acetoxybenzoate hydrochloride crystal provided by the present invention as described above for the preparation of a medicament for the indication treated by an acetylsalicylic acid.

In another preferred embodiment, said acetylsalicylic acid indication is selected from cold and fever, headache, neuralgia, muscle pain, dysmenorrhea, rheumatism, rheumatoid arthritis, gout, cancer, diabetes, diabetic complications, cardiovascular and cerebrovascular diseases, prevention of stroke, prevention of ischemic heart disease, prevention of transient cerebral ischemia, prevention of myocardial embolism, reduction of the incidence and mortality of arrhythmia.

In another preferred embodiment, the dosage form of said medicament is an oral dosage form or a transdermal dosage form; and is more preferably selected from oral solution, capsule, tablet, solution, emulsion, ointment, latex, gel dosage forms.

In a fifth aspect of the present invention, there is provided a pharmaceutical composition, said pharmaceutical composition containing a therapeutically effective amount of the 2-(diethylamino)ethyl 2-acetoxybenzoate hydrochloride crystals provided by the present invention as described above and a pharmaceutically acceptable carrier;

In another preferred embodiment, the dosage form of said pharmaceutical composition is an oral dosage form or a transdermal dosage form; and more preferably, the dosage form of said pharmaceutical composition is selected from oral solution, capsule, tablet, solution, emulsion, ointment, latex, gel dosage forms.

In a sixth aspect of the present invention, there is provided a method for preparing a pharmaceutical composition, said method comprising the steps of: mixing a therapeutically effective amount of the 2-(diethylamino)ethyl 2-acetoxybenzoate hydrochloride crystals provided by the present invention as described above with a pharmaceutically acceptable carrier to obtain the pharmaceutical composition.

Accordingly, the present invention provides a new crystal form of 2-(diethylamino)ethyl 2-acetoxybenzoate hydrochloride.

DETAILED DESCRIPTION

Identification and Properties of
2-(diethylamino)ethyl 2-acetoxybenzoate
Hydrochloride Crystal The properties of 2-(diethylamino)ethyl 2-acetoxybenzoate hydrochloride crystal provided by the present invention are studied by a variety of methods and instruments.

"X-ray powder diffraction (XRPD)" is a common test method for the determination of a crystal structure (i.e., a crystal form). With an X-ray powder diffractometer, a range of diffraction patterns are produced when an X-ray transmits through the crystal, and the various diffraction lines and intensities thereof in the spectrum are determined by atomic groups of a certain structure, thus determining the specific crystallographic structure of the crystal.

The X-ray powder diffraction method for determining a crystal is known in the art. The 2-(diethylamino)ethyl 2-acetoxybenzoate hydrochloride crystal of the present invention has a particular crystal morphology and has particular characteristic peaks in the X-ray powder diffraction (XRPD) pattern. In particular, the X-ray powder diffraction (XRPD) pattern of the 2-(diethylamino)ethyl 2-acetoxybenzoate hydrochloride crystal of the present invention has characteristic peaks at the following 2θ angles: 11.0°±0.2°, 20.6°±0.2°, 25.1°±0.2°, 8.2°±0.2°, 16.5°±0.2°, 13.4°±0.2°, and 25.4°±0.2°; In a preferred embodiment, the pattern further has a characteristic peak at the following 2θ angle: 10.8°±0.2°; In a more preferred embodiment, the pattern further has a characteristic peak at the following 2θ angle: 22.8°±0.2°, 30.4°±0.2°, 19.2°±0.2°, 17.6°±0.2°, 10.6°±0.2°, 23.0°±0.2°, 35.7°±0.2°, 27.9°±0.2°, 18.2°±0.2°, 24.8°±0.2°, and 22.1°±0.2°; and more preferably, the detailed data of the X-ray powder diffraction result of said 2-(diethylamino) ethyl 2-acetoxybenzoate hydrochloride crystal is shown in Table 1, the measurement parameters used including:
  measurement conditions: Cu-Kα;
  a tube voltage/tube current: 40 kV/40 mA;
  and a scanning angle: 3.0221°-44.9861°

TABLE 1

| Pos. [°2θ] | Height [cts] | FWHM [°2θ] | d-spacing (Å) | Rel.Int. [%] |
|---|---|---|---|---|
| 6.0432 | 183.35 | 0.6140 | 14.62543 | 0.11 |
| 7.7771 | 405.94 | 0.0768 | 11.37539 | 0.25 |
| 8.1931 | 13585.52 | 0.0768 | 1.0.79178 | 8.47 |
| 9.9024 | 424.32 | 0.0768 | 8.93248 | 0.26 |
| 10.6619 | 3954.37 | 0.0512 | 8.29785 | 2.46 |
| 10.8178 | 22217.90 | 0.0512 | 8.17859 | 13.85 |
| 10.9820 | 160469.90 | 0.0768 | 8.05663 | 100.00 |
| 12.1649 | 319.04 | 0.1023 | 7.27579 | 0.20 |
| 13.0514 | 424.46 | 0.0768 | 6.78352 | 0.26 |
| 13.3820 | 8706.58 | 0.0768 | 6.61666 | 5.43 |
| 14.7527 | 996.54 | 0.1023 | 6.00481 | 0.62 |
| 16.4440 | 10089.96 | 0.1073 | 5.39083 | 6.29 |
| 17.6799 | 4424.79 | 0.1023 | 5.03080 | 2.76 |
| 18.1873 | 2837.45 | 0.0768 | 4.87784 | 1.77 |
| 18.3594 | 1204.00 | 0.0768 | 4.83251 | 0.75 |
| 19.1131 | 6317.74 | 0.1535 | 4.64362 | 3.94 |
| 20.6050 | 30609.45 | 0.1023 | 4.31065 | 19.07 |
| 20.8585 | 917.22 | 0.0768 | 4.75887 | 0.57 |
| 21.3774 | 239.52 | 0.1023 | 4.15660 | 0.15 |
| 21.8605 | 908.06 | 0.0768 | 4.06582 | 0.57 |
| 27.0537 | 2777.96 | 0.1023 | 4.03071 | 1.39 |
| 22.8211 | 7308.31 | 0.0768 | 3.89681 | 4.55 |
| 22.9649 | 3588.14 | 0.0512 | 3.87273 | 2.24 |
| 24.4819 | 1837.34 | 0.1.279 | 3.63610 | 1.14 |
| 24.7954 | 2603.47 | 0.102.3 | 3.59083 | 1.62 |
| 75.2273 | 18033.81 | 0.1023 | 3.53032 | 11.24 |
| 25.5034 | 7511.72 | 0.0768 | 3.49777 | 4.69 |
| 27.1012 | 936.29 | 0.1279 | 3.29032 | 0.58 |
| 27.7878 | 2907.94 | 0.0768 | 3.21057 | 1.81 |
| 28.4266 | 5072.91 | 0.1279 | 3.13986 | 3.16 |
| 28.9055 | 677.50 | 0.0768 | 3.08892 | 0.42. |
| 29.7455 | 1499.25 | 0.1023 | 3.00358 | 0.93 |
| 30.4088 | 6853.54 | 0..1779 | 7.93956 | 4.27 |
| 30.7641 | 501.17 | 0.1535 | 2.90641 | 0.31 |
| 31.0812 | 899.80 | 0.1023 | 2.87748 | 0.56 |
| 31.3396 | 1164.95 | 0.11023 | 2.85434 | 0.73 |
| 32.3871 | 131.91 | 0.1535 | 2.76437 | 0.08 |
| 32.8991 | 459.99 | 0.1073 | 2.77751 | 0.29 |
| 33.4690 | 857.19 | 0.0768 | 2.67745 | 0.53 |
| 34.0464 | 983.45 | 0.1023 | 2.63333 | 0.61 |
| 35.7734 | 773.04 | 0.1023 | 2.54451 | 0.48 |
| 35.7178 | 7978.47 | 0.1023 | 2.51386 | 1.86 |
| 36.2315 | 104.82 | 0.1.535 | 2.47939 | 0.07 |
| 37.1245 | 1326.51 | 0.0768 | 2.42178 | 0.83 |
| 37.4218 | 945.71 | 0.0768 | 7.40322 | 0.59 |
| 38.3098 | 104.09 | 0.1535 | 2.34953 | 0.06 |
| 39.0969 | 70.21 | 0.1535 | 2.30403 | 0.04 |
| 39.7618 | 775.85 | 0.1791 | 2.76707 | 0.17 |
| 41.2417 | 1300.20 | 0.1791 | 2.18903 | 0.81 |
| 43.6508 | 1385.75 | 0.0936 | 2.07192 | 0.86 |

The 2-(diethylamino)ethyl 2-acetoxybenzoate hydrochloride crystal of the present invention may also be detected using infrared spectroscopy (IR), and the determination method therefor is known in the art. The infrared spectroscopy of the crystal exhibits absorption peaks at 2988.0 $cm^{-1}$, 2974.6 $cm^{-1}$, 2953.7 $cm^{-1}$, 2889.1 $cm^{-1}$, 1725.9 $cm^{-1}$, 1759.1 $cm^{-1}$, 1605.6 $cm^{-1}$, 1576.1 $cm^{-1}$, 1484.0 $cm^{-1}$, 1448.2 $cm^{-1}$, 1389.9 $cm^{-1}$, 1068.7 $cm^{-1}$, 1087.1 $cm^{-1}$, 757.0 $cm^{-1}$, and a range of 2487.3 $cm^{-1}$-2563.4 $cm^{-1}$. An infrared spectroscopy substantially the same as that in FIG. 1 is preferred.

"X-ray single crystal diffraction" is an experimental method for determining the structure of a crystal by diffraction effect of a single crystal on X-rays. The 2-(diethylamino)ethyl 2-acetoxybenzoate hydrochloride crystal provided by the present invention is determined by X-ray single crystal diffraction, the main characteristics thereof comprising:
  a orthorhombic form;
  lattice parameters: a=16.01 Å±0.01 Å, b=7.17 Å±0.01 Å, c=28.86 Å±0.01 Å, and α=β=γ=90°.

In a preferred embodiment, the main characteristics of the 2-(diethylamino)ethyl 2-acetoxybenzoate hydrochloride crystal determined by the X-ray single crystal diffraction further comprise:
  a crystallographic space group: Pbca;
  a unit lattice volume: V=3311.4 Å³±1.0 Å³;
  a crystal size: 0.211×0.176×0.112 mm3;
  a crystal density: 1.267 mg/m3;
  a number of asymmetrical units in lattice: 8; and
  a number of electrons in a unit cell: F(0000)=1344.

Figure 2:
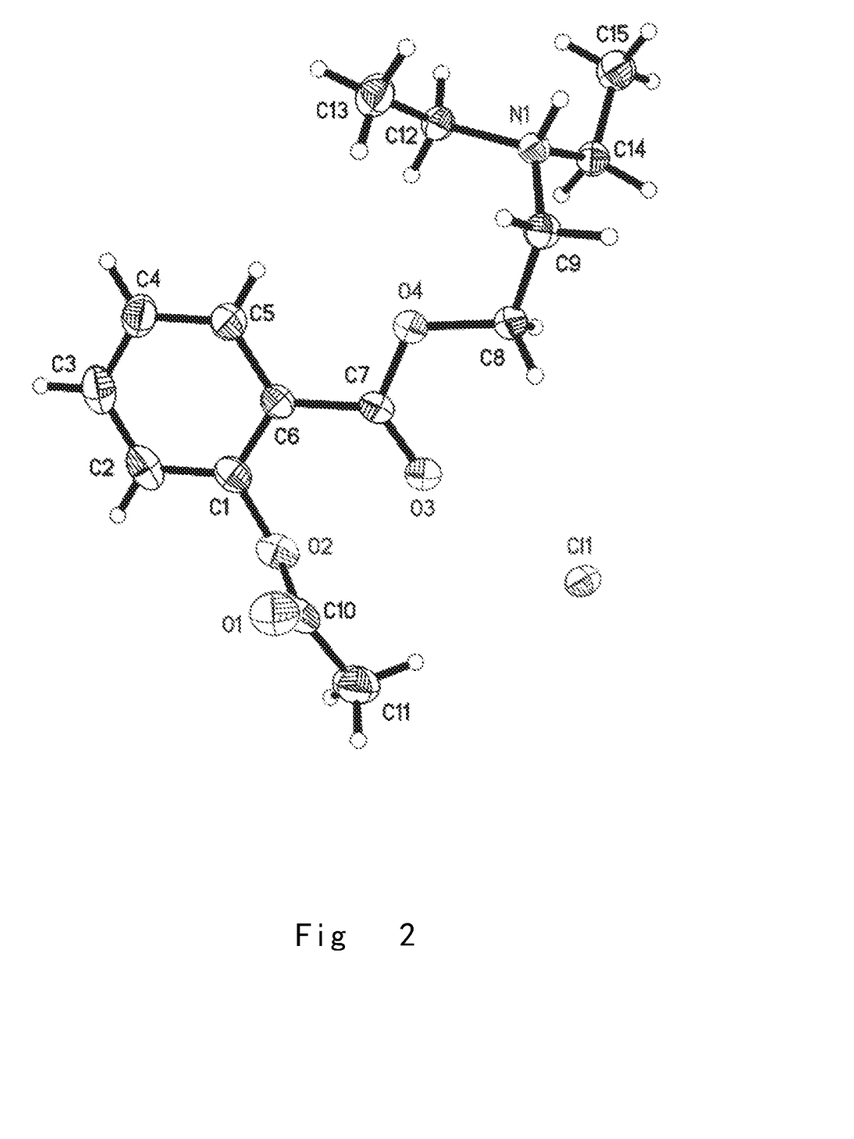
FIG. 2 shows a structure diagram, by the X-ray single crystal diffraction, of the 2-(diethylamino)ethyl 2-acetoxybenzoate hydrochloride crystal as described in the present invention.

In another preferred embodiment, the structure diagram, as determined by the X-ray single crystal diffraction, of said 2-(diethylamino)ethyl 2-acetoxybenzoate hydrochloride crystal is substantially the same as that in FIG. 2.

In a more preferred embodiment, the range of angles for data collection as set for said X-ray single crystal diffraction is 1.895°-25.997°.

The 2-(diethylamino)ethyl 2-acetoxybenzoate hydrochloride crystal provided by the present invention has the advantage of a high purity (99.3%), good stability, etc.

Method for Preparing 2-(diethylamino)ethyl 2-acetoxybenzoate Hydrochloride Crystal In order to obtain the 2-(diethylamino)ethyl 2-acetoxybenzoate hydrochloride crystal described in the present invention, the present inventor has tried many times and the crystallization effects are all unsatisfactory, the specific results being as follows:

(a) 10 g of a crude 2-(diethylamino)ethyl 2-acetoxybenzoate hydrochloride raw material is taken, added to 20-30 ml of dichloromethane for complete solution, a n-hexane or petroleum ether solution is slowly added under stirring, and a white solid is precipitated slowly, but the crystal form of the solid is not good.

(b) 10 g of a crude 2-(diethylamino)ethyl 2-acetoxybenzoate hydrochloride raw material is taken, added to 5-15 ml of dichloromethane, and heated to reflux for 1 hour so that the raw material is completely dissolved; after having been cooled slowly to room temperature, no solid is precipitated, and after the solution is left to stand under freezing conditions of −20° C. for 24 hours or more, a small amount of solid is precipitated, but the crystal form of the solid is not good.

(c) 10 g of a crude 2-(diethylamino)ethyl 2-acetoxybenzoate hydrochloride raw material is taken, added to and dissolved in 25 ml of ethanol, and heated to 50° C., the raw material is dissolved slowly, and after cooled to room temperature, no solid or a small amount of solid is precipitated.

The present inventor finally determines a method for preparing a 2-(diethylamino)ethyl 2-acetoxybenzoate hydrochloride crystal by continuous selections and optimization, with a good crystallization effect and a high efficiency, said method comprising the following steps:

Step I. mixing a crude 2-(diethylamino)ethyl 2-acetoxybenzoate hydrochloride raw material with anhydrous acetonitrile, and completely dissolving the raw materials to obtain a solution; and Step II. cooling the solution to precipitate a white crystal.

In Step I mentioned above, the crude 2-(diethylamino) ethyl 2-acetoxybenzoate hydrochloride raw material and the anhydrous acetonitrile are mixed and then heated to a reflux temperature so that the crude 2-(diethylamino)ethyl 2-acetoxybenzoate hydrochloride raw material is completely dissolved; and the final mass-volume ratio of the crude 2-(diethylamino)ethyl 2-acetoxybenzoate hydrochloride raw material to the added anhydrous acetonitrile is in a range of 1: 2-1:20 w/v, preferably 1: 4-1:10 w/v.

In an embodiment, the solution is obtained by the continuous addition of the anhydrous acetonitrile and the crude 2-(diethylamino)ethyl 2-acetoxybenzoate hydrochloride raw material under heating conditions with stirring and mixing until the crude 2-(diethylamino)ethyl 2-acetoxybenzoate hydrochloride raw material is completely dissolved.

In Step II mentioned above, the solution is cooled to 0-30° C., preferably to 4-25° C.

In a more preferred embodiment, the white crystal obtained in Step II is filtered and dried. Suction filtration is used for said filtration method; and said drying is carried out by vacuum drying, more preferably rotary vacuum drying.

The crude 2-(diethylamino)ethyl 2-acetoxybenzoate hydrochloride raw material involved in the above-mentioned preparation method provided in the present invention can be obtained by conventional methods in the art, and the parameters involved in these methods can be determined by a person skilled in the art through limited trials. Said methods for obtain the raw material include, but not limited to, (1) Aspirin as a raw material is reacted with thionyl chloride under the action of a catalyst to obtain o-acetylsalicyl chloride, the o-acetylsalicyl chloride is reacted with diethylamino ethanol to produce 2-(diethylamino)-ethyl 2-acetoxybenzoate, and finally the 2-(diethylamino)-ethyl 2-acetoxybenzoate is reacted with a hydrogen chloride gas to obtain the crude 2-(diethylamino)ethyl 2-acetoxybenzoate hydrochloride raw material. The reaction process is as shown in formula III. In the formula, said catalyst in said step of reaction with thionyl chloride is selected from, but not limited to, N,N-dimethylformamide, pyridine, and N,N-diisopropylethylamine, the reaction temperature is more preferably in a range of 40° C.-60° C., and the equivalent ratio of the aspirin to the thionyl chloride is more preferably 1:1.1. In said step of reaction with diethylaminoethanol, the reaction equivalent ratio of the diethylaminoethanol to the acetylsalicyl chloride is more preferably 1:1, the reaction temperature is more preferably in a range of 10°° C.-30° C., the reaction time is more preferably 2-6 hours, more preferably, a methyl tert-butyl ether is used as an extraction solvent after the completion of the reaction with diethylaminoethanol, the pH of the solution is adjusted to alkaline (preferably to 7.1-10.0, more preferably to 8.0-9.0), and ice-bath extraction is carried out. In said step of reaction with the hydrogen chloride gas, more preferably, it is required to control the amount of the introduced hydrogen chloride gas, so that the pH range of the reaction liquid is pH 3.0-4.0.

(2) Aspirin as a raw material is subjected to dehydration with diethylaminoethanol under the action of a dehydrating agent to produce 2-(diethylamino)-ethyl 2-acetoxybenzoate, and subsequently the 2-(diethylamino)-ethyl 2-acetoxybenzoate is reacted with a hydrogen chloride gas to obtain the crude 2-(diethylamino)ethyl 2-acetoxybenzoate hydrochloride raw material. The reaction process is as shown in formula IV. In the formula, said dehydrating agent in said step of the reaction of aspirin and diethylaminoethanol is selected from, but not limited to, N,N-dicyclohexylcarbodiimide (DCC), N,N'-diisopropylcarbodiimide (DIC), and 4-dimethylaminopyridine (DMAP). In the process, the final product yield can be improved by adjusting the reaction temperature, the reaction time, the catalyst and other conditions. A person skilled in the art can determine the reaction temperature, the reaction time, whether there is need for and how to select a catalyst, and other conditions required for each step through limited trials.

(3) Aspirin as a raw material is reacted with diethylamino bromoethane under the action of a catalyst to produce 2-(diethylamino)-ethyl 2-acetoxybenzoate, and subsequently the 2-(diethylamino)-ethyl 2-acetoxybenzoate is reacted with a hydrogen chloride gas to obtain the crude 2-(diethylamino)ethyl 2-acetoxybenzoate hydrochloride raw material. The reaction process is as shown in formula V. In the formula, the catalyst used in said step of the reaction of aspirin and ethylamino bromoethane is selected from, but not limited to, cesium carbonate, potassium carbonate, sodium carbonate, triethylamine, and pyridine. In the process, the final product yield can be improved by adjusting the reaction temperature, the reaction time, the catalyst and other conditions. A person skilled in the art can determine the reaction temperature, the reaction time, whether there is need for and how to select a catalyst, and other conditions required for each step through limited trials.

Use and Composition of 2-(diethylamino)ethyl 2-acetoxybenzoate Hydrochloride Crystal According to the contents disclosed in the Chinese patent CN 101484415 B, the 2-(diethylamino)ethyl 2-acetoxybenzoate hydrochloride prepared by the present invention can be used for the treatment of any acetylsalicylic acid (aspirin) indication by oral or transdermal administration, preferably transdermal administration which can reduce common aspirin gastrointestinal side effects. The 2-(diethylamino)ethyl 2-acetoxybenzoate hydrochloride crystal prepared by the present invention can be easily stored and used and has a high purity (99.3%); and can be therefore provided as an active pharmaceutical ingredient or is prepared as a medicament for the prevention or treatment of a variety of diseases against which acetylsalicylic acid can work effectively. In the use, said diseases against which acetylsalicylic acid can work effectively are selected from cold and fever, headache, neuralgia, muscle pain, dysmenorrhea, rheumatism, rheumatoid arthritis, gout, cancer, diabetes, diabetic complications, cardiovascular and cerebrovascular diseases, prevention of stroke, prevention of ischemic heart disease, prevention of transient cerebral ischemia, prevention of myocardial embolism, reduction of the incidence and mortality of arrhythmia.

Therefore, the present invention further relates to a pharmaceutical composition comprising the 2-(diethylamino) ethyl 2-acetoxybenzoate hydrochloride crystals of the present invention, wherein said pharmaceutical composition containing a therapeutically effective amount of the 2-(diethylamino)ethyl 2-acetoxybenzoate hydrochloride crystals and a pharmaceutically acceptable carrier.

As used herein, the term "containing" or "comprising" includes "including", "essentially consisting of" and "consisting of". The term "a therapeutically effective amount" refers to an amount which can be functional or active to human and/or animals and can be acceptable by human and/or animals.

As used herein, the term "pharmaceutically acceptable" refers to a substance which is suitable for use in human and/or animals without significant adverse effects (e.g., toxicity, irritation, and allergic reactions), i.e., a substance that has a reasonable benefit/risk ratio. The term "pharmaceutically acceptable carrier" refers to a carrier with which a therapeutic agent is administrated, including various excipients and diluents. The term refers to some agent carriers which are not essential active ingredients themselves and are not overly toxic after administration. Suitable carriers are well known to a person of ordinary skill in the art. A full discussion of pharmaceutically acceptable excipients can be found in Remington's Pharmaceutical Sciences, Mack Pub. Co., N.J. 1991.

Preferably, said "pharmaceutically acceptable carrier" is selected from fillers, disintegrants, lubricants, glidants, effervescent agents, flavouring agents, coating materials, excipients, or sustained/controlled release agents. In a composition, the pharmaceutically acceptable carrier may contain liquids such as water, saline, glycerol and ethanol. In addition, auxiliary substances such as fillers, disintegrants, lubricants, glidants, effervescent agents, wetting or emulsifying agents, flavouring agents, pH buffering substances, etc., may also be present in these carriers. In general, these materials may be formulated in non-toxic, inert and pharmaceutically acceptable aqueous carrier media.

Moreover, the dosage forms of the pharmaceutical composition described in the present invention is preferably oral and transdermal dosage forms such as oral solution, capsule, tablet, solution, emulsion, ointment, latex, and gel dosage forms.

The features mentioned above in the present invention, or the features mentioned in the embodiments, may be combined in any way. All the features revealed in the description of this case may be used in combination in any form of composition, and the various features revealed in the description may be substituted with any alternative features that can achieve the same, equivalent or similar purposes. Therefore, unless otherwise specified, the revealed features are merely general examples of equivalent or similar features.

The main advantages of the present invention lie in:

1. A stable 2-(diethylamino)ethyl 2-acetoxybenzoate hydrochloride crystal is obtained for the first time, which is an important measure to ensure that the quality is controllable when a medicament is prepared from the compound.

2. The method for preparing the 2-(diethylamino)ethyl 2-acetoxybenzoate hydrochloride crystal crystals provided by the present invention has a low energy consumption and a stable yield and is easy for industrial production.

The invention is further described in conjunction with particular examples. It is to be understood that these examples are merely illustrative of the invention rather than limiting the scope of the invention. Experimental methods without specific conditions specified in the following examples are generally carried out in accordance with conventional conditions or in accordance with conditions recommended by the manufacturers. Unless otherwise stated, all percentages, ratios, proportions, or parts are by weight.

The unit of the weight volume percentages in the present invention is well known to a person skilled in the art and refers, for example, to the weight of a solute in 100 mL of a solution.

Unless otherwise defined, all professional and scientific terms used herein are of the same meaning to those skilled in the art are familiar with. In addition, any methods and materials similar to or equivalent to those in the contents as disclosed may be applied to the method of the present invention. The preferred implementation methods and materials described herein are for exemplary purposes only.

Example 1

Preparation of 2-(diethylamino)ethyl 2-acetoxybenzoate Hydrochloride Crystal a. Preparation of Crude 2-(diethylamino)ethyl 2-acetoxybenzoate Hydrochloride Raw Material With toluene as a solvent and N,N-dimethylformamide as a catalyst, aspirin is reacted with thionyl chloride in an equivalent ratio of 1:1.1 under the conditions of a reaction temperature of 50° C. for 2 hours to produce o-acetylsalicyl chloride; next, diethylaminoethanol is reacted with the acylate o-acetylsalicyl chloride in an equivalent ratio of 1:1 at a reaction temperature of 25° C. for 4 hours to produce 2-(diethylamino)-ethyl 2-acetoxybenzoate; the aqueous phase is extracted with methyl tert-butyl ether, and the aqueous phase is taken and adjusted to alkaline in an ice bath; the aqueous phase is then extracted with isopropyl acetate as an extractant, and the isopropyl acetate phase is taken; and isopropyl acetate is used as a solvent in the salt forming process, and subsequently the introduction amount of hydrogen chloride gas is strictly controlled so that the pH of the reaction liquid is about 3.5. After the completion of the reaction, the crude 2-(diethylamino)ethyl 2-acetoxybenzoate hydrochloride raw material is obtained.

b. Preparation of 2-(diethylamino)ethyl 2-acetoxybenzoate Hydrochloride Crystal

Under conditions of reflux heating, anhydrous acetonitrile is added into a crude 2-(diethylamino)ethyl 2-acetoxybenzoate hydrochloride crystal raw material continuously with stirring and mixing until the 2-(diethylamino)ethyl 2-acetoxybenzoate hydrochloride is completely dissolved. In the process, the final mass-volume ratio of the crude 2-(diethylamino)ethyl 2-acetoxybenzoate hydrochloride raw material to the anhydrous acetonitrile is 1:4. After having been cooled slowly to 25° C., a white crystal is precipitated, and after suction filtration, the solid is subjected to rotary vacuum drying.

Example 2

X-Ray Powder Diffraction Determination of 2-(diethylamino)ethyl 2-Acetoxybenzoate Hydrochloride Crystal The 2-(diethylamino)ethyl 2-acetoxybenzoate hydrochloride crystal obtained in Example 1 is taken and subjected to X-ray powder diffraction determination with a detection instrument: Panalytical X'Pert Powder Power X-Ray Diffractometer; measurement conditions: Cu-Kα; a tube voltage/tube current: 40 kV/40 mA; a scanning angle: 3.0221°-44.9861°; a scanning step: 0.0260°; an emission slit: 0.2177; and a test temperature: 25° C.

The resulting data is as shown in Table 1.

TABLE 1

| Pos. [°2θ] | Height [cts] | FWHM [°2θ] | d-spacing (Å) | Rel.Int. [%] |
|---|---|---|---|---|
| 6.0432 | 183.35 | 0.6140 | 14.62543 | 0.11 |
| 7.7721 | 405.94 | 0.0768 | 11.37539 | 0.75 |
| 8.1931 | 13585.52 | 0.0768 | 10.79178 | 8.47 |
| 9.9024 | 474.32 | 0.0768 | 8.93248 | 0.26 |
| 10.6619 | 3954.37 | 0.0512. | 8.29785 | 2.46 |
| 10.8178 | 22217.90 | 0.0512 | 8.17859 | 13.85 |
| 10.9820 | 160469.90 | 0.0768 | 8.05663 | 100.00 |
| 12.1649 | 319.04 | 0.1023 | 7.27579 | 0.20 |
| 13.0514 | 424.46 | 0.0768 | 6.78352 | 0.26 |
| 13.3820 | 8706.58 | 0.0768 | 6.61666 | 5.43 |
| 14.7527 | 996.54 | 0.1023 | 6.00481 | 0.62 |
| 16.4440 | 10089.96 | 0.1023 | 5.39083 | 6.29 |
| 17.6299 | 4424.79 | 0.1023 | 5.03080 | 2.76 |
| 18.1873 | 2837.45 | 0.0768 | 4.87784 | 1.77 |
| 18.3594 | 1204.00 | 0.0768 | 4.83251 | 0.75 |
| 19.1131 | 6317.74 | 0.1535 | 4.64362 | 3.94 |
| 20.6050 | 30609.45 | 0.1023 | 4.31065 | 19.07 |
| 20.8585 | 917.77 | 0.0768 | 4.25882 | 0.57 |
| 21.3774 | 239.52 | 0.1023 | 4.15660 | 0.15 |
| 21.8605 | 908.06 | 0.0768 | 4.06587 | 0.57 |
| 22.0532 | 2222.96 | 0.1023 | 4.03073 | 1.39 |
| 27.8211 | 7308.31 | 0.0768 | 3.89681 | 4.55 |
| 22.9649 | 3588.14 | 0.0512 | 3.87273 | 2.24 |
| 24.4819 | 1837.34 | 0.1279 | 3.63610 | 1.14 |
| 24.7954 | 2603.47 | 0.1073 | 3.59083 | 1.67 |
| 25.2273 | 18033.81 | 0.1023 | 3.53032 | 11.24 |
| 25.5034 | 7521.22 | 0.0768 | 3.49272 | 4.69 |
| 27.1012 | 936.29 | 0.1279 | 3.29032 | 0.58 |
| 27.7878 | 2907.94 | 0.0768 | 3.21057 | 1.81 |
| 28.4266 | 5072.91 | 0.1279 | 3.13986 | 3.16 |
| 28.9055 | 677.50 | 0.0768 | 3.08892 | 0.42 |
| 29.7455 | 1499.25 | 0.1023 | 3.00358 | 0.93 |
| 30.4088 | 6853.54 | 0.1279 | 2.93956 | 4.27 |
| 30.7641 | 501.17 | 0.1535 | 2.90641 | 0.31 |

TABLE 1-continued

| Pos. [°2θ] | Height [cts] | FWHM [°2θ] | d-spacing (Å) | Rel.Int. [%] |
|---|---|---|---|---|
| 31.0812 | 899.80 | 0.1023 | 2.87748 | 0.56 |
| 31.3396 | 1164.95 | 0.1023 | 2.85434 | 0.73 |
| 32.3871 | 131.91 | 0.1535 | 2.76437 | 0.08 |
| 32.8991 | 459.99 | 0.1023 | 2.71151 | 0.29 |
| 33.4690 | 857.19 | 0.0768 | 2.67745 | 0.53 |
| 34.0464 | 983.45 | 0.1023 | 2.63335 | 0.61 |
| 35.2734 | 773.04 | 0.1023 | 2.54451 | 0.48 |
| 35.7178 | 2978.47 | 0.1023 | 2.51386 | 1.86 |
| 36.2315 | 104.82 | 0.1535 | 2.47939 | 0.07 |
| 37.1245 | 1326.51 | 0.0768 | 2.42178 | 0.83 |
| 37.4218 | 945.71 | 0.0768 | 2.40322 | 0.59 |
| 38.3098 | 104.09 | 0.1535 | 2.34953 | 0.06 |
| 39.0969 | 70.11 | 0.1535 | 2.30403 | 0.04 |
| 39.7618 | 275.85 | 0.1791 | 2.26702 | 0.17 |
| 41.2417 | 1300.20 | 0.1791 | 2.18903 | 0.81 |
| 43.6508 | 1385.75 | 0.0936 | 2.07192 | 0.86 |

Example 3

X-Ray Single Crystal Diffraction Determination of 2-(diethylamino)ethyl 2-Acetoxybenzoate Hydrochloride Crystal The 2-(diethylamino)ethyl 2-acetoxybenzoate hydrochloride crystal obtained in Example 1 is taken and subjected to X-ray single crystal diffraction determination with an instrument: Bmker SMART APEX CCD single crystal diffractometer; a test temperature: 293 K; a scanning wavelength: 0.71073 Å; a absorption correction factor: 0.243 mm-1; a range of angles for data collection: 1.895°-25.997°; a diffraction index range: $-17<=h<=19$, $-8<=k<=8$, $-24<=1<=35$. The structure diagram is shown in FIG. 2. The resulting characteristic data are characterized as follows:

an orthorhombic form;
lattice parameters: a=16.0138 Å, b=7.1652 Å, c=28.8590 Å, and α=β=γ=90°.
a crystallographic space group: Pbca;
a unit lattice volume: V=3311.4 Å3;
a crystal size: 0.211×0.176×0.112 mm3;
a crystal density: 1.267 mg/m3;
a number of asymmetrical units in lattice: 8; and
a number of electrons in a unit cell: F(0000)=1344.

Example 4

Preparation of 2-(diethylamino)ethyl 2-acetoxybenzoate Hydrochloride Crystal a. Preparation of Crude 2-(diethylamino)ethyl 2-acetoxybenzoate Hydrochloride Raw Material Aspirin as a raw material in trichloromethane as a solvent in the presence of N,N-dicyclohexylcarbodiimide as a dehydrating agent (the equivalent ratio of the aspirin to the N,N-dicyclohexylcarbodiimide being 1:2) is reacted with diethylaminoethanol in an equivalent ratio of 1:1.2 to produce 2-(diethylamino)ethyl 2-acetoxybenzoate hydrochloride, followed by the introduction of a hydrogen chloride gas, with the introduction amount of the hydrogen chloride gas in the reaction process strictly controlled so that the pH is about 3.0. After the reaction, the crude 2-(diethylamino) ethyl 2-acetoxybenzoate hydrochloride raw material is obtained.

b. Preparation of 2-(diethylamino)ethyl 2-acetoxybenzoate Hydrochloride Crystal

Under conditions of heating, an anhydrous acetonitrile solution is added into a crude 2-(diethylamino)ethyl 2-acetoxybenzoate hydrochloride raw material continuously with stirring and mixing until the 2-(diethylamino)ethyl 2-acetoxybenzoate hydrochloride is completely dissolved, wherein the final mass-volume ratio of the crude 2-(diethylamino)ethyl 2-acetoxybenzoate hydrochloride raw material to the anhydrous acetonitrile is 1:10. After having been cooled slowly to 4° C., a white crystal is precipitated, and after suction filtration, the solid is subjected to rotary vacuum drying.

Example 5

Infrared Absorption Spectrum Determination of 2-(diethylamino)ethyl 2-Acetoxybenzoate Hydrochloride Crystal The 2-(diethylamino)ethyl 2-acetoxybenzoate hydrochloride crystal obtained in Example 4 is subjected to infrared absorption spectrum determination with an instrument: Nicolet iZ10 fourier transform infrared spectrometer. A potassium bromide pellet method is used; the number of scanning is 32; the number of background scanning is 32; the resolution ratio is 4.000; the sampling gain is 1.0; and the moving mirror speed is 0.6329. The resulting infrared absorption spectrum is as shown in FIG. 1.

Example 6

Stability Test of 2-(diethylamino)ethyl 2-acetoxybenzoate Hydrochloride Crystal

The 2-(diethylamino)ethyl 2-acetoxybenzoate hydrochloride crystals obtained in Example 1 is taken and placed under the conditions of 25° C.±2° C., and sampling is carried out at month 0, month 3, month 6, month 9, and month 12, respectively, followed by the detection of the pH value, related substances and their contents. In the process, the pH value is obtained by taking about 1.0 g of a sample, adding 50 mL of water, shaking for 10 minutes, filtration, taking 10 mL of a subsequent filtrate and detection with a pH meter; and the related substances and the contents are both detected by high performance liquid chromatography (an external standard method). The results show that the crystal of the present invention after having been stored at 25° C.±2° C. for 12 months has a very good stability. The specific data are shown in Table 2.

TABLE 2

|  | Detection item | Month 0 | Month 3 | Month 6 | Month 9 | Month 12 |
|---|---|---|---|---|---|---|
|  |  |  |  | pH value |  |  |
|  |  | 4.82 | 4.83 | 4.81 | 4.79 | 4.83 |
| Related substances | 2-(diethylamino)ethyl-salicylate hydrochloride | 0.58% | 0.65% | 0.58% | 0.60% | 0.62% |
|  | Acetylsalicylic acid | 0.0059% | 0.0063% | 0.0070% | 0.0048% | 0.0053% |
|  | Salicylic acid | Not detected | 0.00254% | 0.00101% | 0.00083% | 0.00103% |
|  | Other related substances | Not detected | Not detected | Not detected | Not detected | Not detected |
|  | Content | 99.58% | 99.51% | 99.59% | 99.57% | 99.58% |

The above description is merely illustrative of the preferred embodiments of the present invention rather than limiting the scope of the essential technical contents of the present invention, the essential technical contents of the present invention are broadly defined in the claims of the application; any technical entities or methods that are achieved by other person, if completely the same to that defined in the scope of the claims of the application, is also an equivalent change and shall be regarded as encompassed within the scope of the claims.

What is claimed is:

1. A method for treating indication which can be treated by acetylsalicylic acid, the indication being selected from pain, fevers, cardiovascular and cerebrovascular diseases, and inflammation, the method comprising administering to human in need thereof a therapeutically effective amount of a compound of 2-(diethylamino)ethyl 2-acetoxybenzoate hydrochloride crystal having a chemical structure as represented by formula I, wherein the X-ray powder diffraction (XRPD) pattern of the crystal having characteristic peaks at the following 2θ angles: 11.0°±0.2°, 20.6°±0.2°, 25.1°±0.2°, 8.2°±0.2°, 16.5°±0.2°, 13.4°±0.2°, 25.4°±0.2°;

I

2. The method of claim 1, wherein the indication which can be treated by acetylsalicylic acid is selected from cold, headache, neuralgia, dysmenorrhea, rheumatism, rheumatoid arthritis, gout, diabetes, diabetic complications, prevention of stroke, prevention of ischemic heart disease, prevention of transient cerebral ischemia, prevention of myocardial embolism, and reduction of the incidence and mortality of arrhythmia.

3. A method for preparing the 2-(diethylamino)ethyl 2-acetoxybenzoate hydrochloride crystal, wherein the method comprises the steps of:
(1) mixing a crude 2-(diethylamino)ethyl 2-acetoxybenzoate hydrochloride raw material with anhydrous acetonitrile, and completely dissolving the raw materials to obtain a solution where the final mass-volume ratio of the crude 2-(diethylamino)ethyl 2-acetoxybenzoate hydrochloride raw material to the anhydrous acetonitrile is 1: 4-1:10 w/v; and
(2) cooling the solution to 0-30° C. to precipitate the 2-(diethylamino) ethyl 2-acetoxybenzoate hydrochloride crystal having a chemical structure as represented by formula I, wherein the X-ray powder diffraction (XRPD) pattern of the crystal having characteristic peaks at the following 2θ angles: 11.0°±0.2°, 20.6°±0.2°, 25.1°±0.2°, 8.2°±0.2°, 16.5°±0.2°, 13.4°±0.2°, 25.4°±0.2°.

4. The method of claim 3, wherein heating to refluxing anhydrous acetonitrile is required in the dissolution process.

5. The method of claim 1, wherein the X-ray powder diffraction (XRPD) pattern of the crystal further having a characteristic peak at the following 2θ angle: 10.8°±0.2°.

6. The method of claim 1, wherein the X-ray powder diffraction (XRPD) pattern of the crystal further having characteristic peaks at the following 2θ angles: 22.8°±0.2°, 30.4°±0.2°, 19.2°±0.2°, 17.6°±0.2°, 10.6°±0.2°, 23.0°±0.2°, 35.7°±0.2°, 27.9°±0.2°, 18.2°±0.2°, 24.8°±0.2°, 22.1°±0.2°.

7. The method of claim 1, wherein the infrared absorption spectrum of the crystal having absorption peaks at 2988.0 cm$^{-1}$, 2974.6 cm$^{-1}$, 2953.7 cm$^{-1}$, 2889.1 cm$^{-1}$, 1725.9 cm$^{-1}$, 1759.1 cm$^{-1}$, 1605.6 cm$^{-1}$, 1576.1 cm$^{-1}$, 1484.0 cm$^{-1}$, 1448.2 cm$^{-1}$, 1389.9 cm$^{-1}$, 1068.7 cm$^{-1}$, 1087.1 cm$^{-1}$, 757.0 cm$^{-1}$, and in a range of 2487.3 cm$^{-1}$ to 2563.4 cm$^{-1}$.

8. The method of claim 1, wherein the crystal being orthorhombic, and having lattice parameters, as determined by X-ray single crystal diffraction: a=16.01 Å±0.01 Å, b=7.17 Å±0.01 Å, c=28.86 Å±0.01 Å, α=β=γ=90°.

9. The method of claim 8, wherein the said crystal further comprising the following characteristics, as determined by X-ray single crystal diffraction:
a crystallographic space group: Pbca;
a unit lattice volume: V=3311.4 Å$^3$±1.0 Å$^3$;
a crystal size: 0.211×0.176×0.112 mm$^3$;
a crystal density: 1.267 mg/m$^3$;
a number of asymmetrical units in lattice: 8;
a number of electrons in a unit cell: F(0000)=1344.

10. The preparation method of claim 3, wherein the X-ray powder diffraction (XRPD) pattern of the crystal further having a characteristic peak at the following 2θ angle: 10.8°±0.2°.

11. The preparation method of claim 3, wherein the X-ray powder diffraction (XRPD) pattern of the crystal further having characteristic peaks at the following 2θ angles: 22.8°±0.2°, 30.4°±0.2°, 19.2°±0.2°, 17.6°±0.2°, 10.6°±0.2°, 23.0°±0.2°, 35.7°±0.2°, 27.9°±0.2°, 18.2°±0.2°, 24.8°±0.2°, 22.1°±0.2°.

* * * * *

UNITED STATES PATENT AND TRADEMARK OFFICE
CERTIFICATE OF CORRECTION

Page 1 of 1

PATENT NO. : 10,882,817 B2
APPLICATION NO. : 16/676575
DATED : January 5, 2021
INVENTOR(S) : Jing Zhang It is certified that error appears in the above-identified patent and that said Letters Patent is hereby corrected as shown below:

On the Title Page

• In the Abstract, chemical structure correct "Chinese Characters" to read as -- formula (I) --.

In the Specification

• Column 8, Line 5, the first chemical structure correct "Chinese Characters" to read as -- thionyl chloride --.

• Column 8, Line 15, the second chemical structure, correct "Chinese Characters" to read as -- diethylaminoethanol --.

• Column 8, Line 60, the last chemical structure, correct "Chinese Characters" to read as -- diethylaminoethanol --.

• Column 9, Line 40, the second chemical structure, correct "Chinese Characters" to read as -- diethylamino bromoethane --.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*